United States Patent [19]
Van Reet et al.

[11] 4,079,062
[45] Mar. 14, 1978

[54] TRIAZOLE DERIVATIVES

[75] Inventors: Gustaaf Van Reet, Tessenderlo; Jan Heeres, Vosselaar; Lourens Wals, Turnhout, all of Belgium

[73] Assignee: Janssen Pharmaceutica N.V., Beerse, Belgium

[21] Appl. No.: 620,989

[22] Filed: Oct. 9, 1975

Related U.S. Application Data

[63] Continuation-in-part of Ser. No. 524,587, Nov. 18, 1974, abandoned.

[51] Int. Cl.$^2$ .......................................... C07D 249/08
[52] U.S. Cl. .................................... 260/308 R; 71/92; 260/332.2 H; 260/340.7; 260/340.9 R; 424/269
[58] Field of Search ...................... 260/308 R; 71/92; 424/269

[56] References Cited

U.S. PATENT DOCUMENTS

| | | | |
|---|---|---|---|
| 3,575,999 | 4/1971 | Godefroi et al. | 260/309 |
| 3,755,349 | 8/1973 | Timmler et al. | 260/308 R |

*Primary Examiner*—R. Gallagher
*Attorney, Agent, or Firm*—Salvatore R. Coate

[57] ABSTRACT

Novel 1-($\beta$-aryl)ethyl-1H-1,2,4-triazole ketals useful for their antimicrobial and plant-growth regulating activities.

6 Claims, No Drawings

TRIAZOLE DERIVATIVES

CROSS-REFERENCE TO RELATED APPLICATION

This is a continuation-in-part of our copending application, Ser. No. 524,587, filed Nov. 18, 1974 now abandoned.

BACKGROUND OF THE INVENTION

In U.S. Pat. No. 3,575,999 there are described 1(β-aryl)-ethyl-imidazole ketals having antibacterial and antifungal properties.

In the prior art there may also be found a number of triazole derivatives, some of which are described as fungicides or growth regulators.

Among other differences the compounds of this invention differ from the triazole derivatives of the prior art by the nature of the side chain which is attached to the triazole nitrogen atom.

The closest prior art on triazole derivatives is tentatively repesented by the following references:
Neth. Pat. Appln. No. 69.13.028; and
Fr. Pat. No. 2.200.012 - Derwent Week V25 - Pharm. p. 7.

DESCRIPTION OF THE PREFERRED EMBODIMENTS:

This invention relates to a novel group of chemical compounds and more particularly to 1H-1,2,4-triazole derivatives having the formula

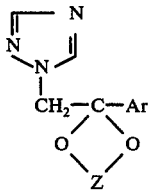
(I)

wherein
Z is an alkylene selected from the group consisting of

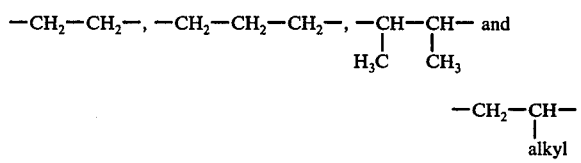

wherein said alkyl has from 1 to about 10 carbon atoms; and

Ar is a member selected from the group consisting of phenyl, substituted phenyl, thienyl, halothienyl, naphthyl and fluorenyl, wherein "substituted phenyl" has the meaning of a phenyl radical having thereon from 1 to 3 substituents selected independently from the group consisting of halo, loweralkyl, loweralkyloxy, cyano and nitro.

The therapeutically active acid addition salts of the foregoing compound (I) are also embraced within the scope of this invention.

As used in the foregoing definition of Z, the term "alkyl" is meant to include straight and branch chained hydrocarbon radicals having from 1 to about 10 carbon atoms, such as, for example, methyl, ethyl, 1-methylethyl, propyl, 1,1-dimethylethyl, butyl, pentyl, hexyl, heptyl, octyl, decyl and the like; as used herein "loweralkyl" may be straight or branch chained saturated hydrocarbons having from 1 to 6 carbon atoms, such as, for example, methyl, ethyl, propyl, 1-methylethyl, butyl, 1,1-dimethylethyl, pentyl, hexyl and the like alkyls; and the term "halo" is generic to halogen atoms of atomic weight less than 127; i.e., fluoro, chloro, bromo and iodo.

The ketals of formula (I) are readily obtained by reacting 1H-1,2,4-triazole (II), previously converted into a metal salt thereof, such as, for example, by treatment with an alkali metal alkoxide, preferably sodium methoxide, with a halide of formula (III)

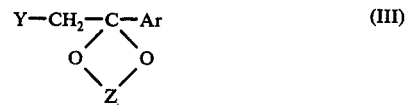
(III)

wherein Ar and Z are as previously defined and Y is halo, preferably bromo. The reaction of 1H-1,2,4-triazole (II) with (III) is preferably carried out in an appropriate polar reaction-inert oganic solvent, such as, for example, N,N-dimethylformamide, N,N-dimethylacetamide, acetonitrile, benzonitrile and the like. Such solvents may be used in combination with other reaction-inert organic solvents, such as, for example, benzene, methylbenzene, dimethylbenzene and the like. When Y stands for bromo or chloro, the addition of an alkali metal iodide, such as, for example, sodium- or potassium iodide is appropriate. Somewhat elevated temperatures are appropriate to enhance the rate of the reaction and most preferably the reaction is carried out at the reflux temperature of the reaction mixture.

The resulting ketal of formula (I) is then isolated from the reaction mixture by conventional means and, if desired, further purified according to common purification procedures such as, for example, crystallization, extraction, trituration, chromatography, etc..

The foregoing procedure is further illustrated by the following schematic representation:

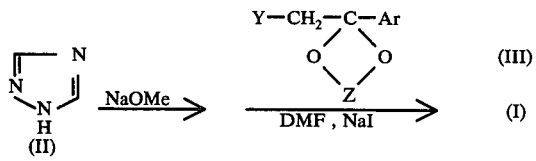

The thus-obtained compounds of formula (I), in base form, may be converted to their therapeutically useful acid addition salts by reaction with an appropriate acid, as, for example, an inorganic acid such as hydrohalic acid, i.e., hydrochloric, hydrobromic or hydroiodic acid; sulfuric, nitric or thiocyanic acid; a phosphoric acid; an organic acid such as acetic, propanoic, hydroxyacetic, α-hydroxypropanoic, 2-oxopropanoic, ethanedioic, propanedioic, 1,4-butanedioic, (Z)-2-butenedioic, (E)-2-butenedioic, 2-hydroxy-1,4-butanedioic, 2,3-dihydroxy-1,4-butanedioic, 2-hydroxy-1,2,3-propanetricarboxylic, benzoic, 3-phenylpropenoic, α-hydroxybenzeneacetic, methanesulfonic, ethanesulfonic, hydroxyethanesulfonic, 4-methylbenzenesulfonic, α-hydroxybenzoic, 4-amino-2-hydroxybenzoic, 2-phenoxybenzoic or 2-acetyloxybenzoic acid. The salts are in turn converted to the corresponding free bases in the usual manner, e.g., by reaction with alkali such as sodium or potassium hydroxide.

The starting materials of formula (III), a number of which are known compounds, may be prepared according to known procedures. Such compounds wherein Z is selected from the group consisting of —CH$_2$—CH$_2$—, —CH(CH$_3$)—CH$_2$, —CH(CH$_3$)—CH(CH$_3$)— and —CH$_2$—CH$_2$—CH$_2$— and methods of preparing the same are described in U.S. Pat. No. 3,575,999. In general the compounds of formula (III) may be prepared by the ketalization of an appropriate ketone of formula (IV) wherein Ar and Y are as previously defined, with an appropriate diol of formula (V) following known ketalization procedures as are described in the literature [see e.g. Synthesis, 1974 (1), 23].

In a preferred method both reactants are refluxed together for several hours with azeotropic water removal in an appropriate organic solvent, preferably in the presence of a simple alcohol, such as, for example, ethanol, propanol, butanol, pentanol and the like, and in the presence of an appropriate strong acid such as, for example, 4-methylbenzenesulfonic acid. Suitable organic solvents which may be used therefore include, for example, aromatic hydrocarbons such as benzene, methylbenzene, dimethylbenzene and the like and saturated hydrocarbons, such as cyclohexane.

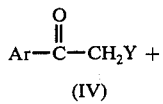

(IV)

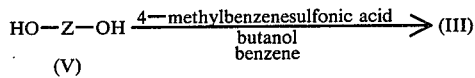

The ketones of formula (IV) are generally known and may be prepared following methodologies known to those skilled in the art.

From formula (I) it is evident that several of the compounds of this invention have asymmetric carbon atoms within their structure and consequently they may exist under different stereochemical optical isomeric forms. More particularly, when an alkylgroup is present in the 4-position of the dioxolanenucleus, the carbon atoms to which it is attached and the carbon atom in the 2-position of the dioxolanenucleus are asymmetric. The stereochemical optical isomers of compounds of formula (I) may be separated and isolated following methodologies known to those skilled in the art. Said isomers are intended to be within the scope of this invention.

The compounds of formula (I) and the acid addition salts thereof are useful agents in combatting fungi and bacteria. As such the compounds of this invention are valuable in the treatment of plants, animals and human beings suffering from pathogenic microorganisms and in the destruction of microorganism on materials.

The compounds of this invention are very potent agricultural fungicides. They are very active against a wide variety of fungi such as, for example, those responsible for the occurence of powdery mildew on different plant species, e.g., *Erysiphe graminis, Erysiphe polygoni, Erysiphe cichoracearum, Erysiphe polyphaga, Podosphaera leuchotricha, Sphaerotheca pannosa, Sphaerotheca mors-uvae, Uncinula necator,* etc., and other fungi, such as, for example, *Venturia inaequalis, Colletotrichum lindemuthianum, Fusarium oxysporum, Alternaria tenuis, Thielaviopsis basicola, Helminthosporium gramineum, Penicillium digitatum,* etc..

They are especially useful in view of their prophylactic as well as curative and systemic action. Their potent antifungal action against phytopathogenic fungi is more clearly illustrated by the results obtained in the following experiments.

In several of these experiments the compound 1-[2-(2,4-dichlorophenyl)-1,3-dioxolan-2-ylmethyl]-1H-1,2,4-triazole, (I-a), was used as a representative member of the compounds of formula (I).

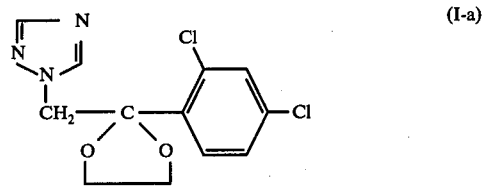

It is understood that the compounds for which experimental test results are presented are not given for the purpose of limiting the invention thereto but only to exemplify the strong antifungal activity of all the compounds within the scope of formula (I).

A. Prophylactic action of compounds of formula (I) against *Erysiphe cichoracearum* on cucumber upon foliar treatment.

Young cucumber plants, about 10 days old, were sprayed with an aqueous solution containing 250, 100 or 10 ppm of the compound to be tested while controls were kept untreated. After drying of the plants, artificial infection with spores of *Erysiphe cichoracearum* was carried out by slightly rubbing the plants with a heavily infected leaf. At the 15 th. day after artificial infection the degree of fungal attack was evaluated by counting the number of spots per plants. The results given in table I are mean values for 2 plants and expressed according to the following score system.

0 = 0 spots per plant.
1 = 1 to 5 spots per plant.
2 = 6 to 10 spots per plant.
3 = more than 10 spots per plant.

TABLE I

Prophylactic action of compounds (I) against *Erysiphe cichoracearum* on cucumber plants upon foliar treatment.

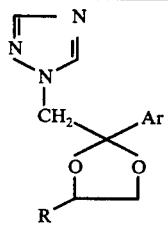

| Ar | R | Base or Salt form | Antifungal score 250 ppm | 100 ppm | 10 ppm |
|---|---|---|---|---|---|
| 2,4-(Cl)₂—C₆H₃ | H | base | — | 0 | 0 |
| C₆H₅ | H | base | — | 3 | — |
| 4-NO₂—C₆H₄ | H | base | 0 | — | — |
| 3-Cl—C₆H₄ | H | base | — | 2 | — |
| 2-Cl—C₆H₄ | H | (COOH)₂ | — | 0 | — |
| 4-Br—C₆H₄ | H | base | 0 | — | — |
| 2-Br—C₆H₄ | H | (COOH)₂ | — | 2 | — |
| 3-OCH₃—C₆H₄ | H | (COOH)₂ | 1 | — | — |
| 2-CH₃—C₆H₄ | H | (COOH)₂ | 0 | — | — |
| 4-F-C₆H₄ | H | (COOH)₂ | 0 | — | — |
| 4-CH₃—C₆H₄ | H | (COOH)₂ | 0 | — | — |
| 4-Cl—C₆H₄ | H | (COOH)₂ · H₂O | — | 0 | — |
| 2-naphthyl | H | (COOH)₂ | 0 | — | — |
| 2,5-(Cl)₂—C₆H₃ | H | (COOH)₂ | — | 0 | — |
| 4-CN—C₆H₄ | H | (COOH)₂ | 0 | — | — |
| 3,4-(Cl)₂—C₆H₃ | H | (COOH)₂ | — | 3 | — |
| 2-OCH₃—C₆H₄ | H | (COOH)₂ | 1 | — | — |
| 2-thienyl | H | (COOH)₂ | — | 2 | — |
| 2-fluorenyl | H | base | 0 | — | — |
| 5-Cl-2-thienyl | H | base | — | 2 | — |
| 3-Br,4-CH₃—C₆H₃ | H | base | 0 | — | — |
| 2-CH₃, 4-Br—C₆H₃ | H | base | — | 2 | — |
| 2-CH₃, 4-Cl—C₆H₃ | H | base | 0 | — | — |
| 3-Br—C₆H₄ | H | base | 2 | — | — |
| 4-I-C₆H₄ | H | (COOH)₂ | 0 | — | — |
| 3,5-(Cl)₂—C₆H₃ | H | (COOH)₂ | — | 2 | — |
| 2,3-(Cl)₂—C₆H₃ | H | (COOH)₂ | 0 | — | — |
| 3-NO₂—C₆H₄ | H | base | 1 | — | — |
| 2,4-(Br)₂—C₆H₃ | H | (COOH)₂ | — | 1 | — |
| 2,4,5-(Cl)₃—C₆H₂ | H | (COOH)₂ | 0 | — | — |
| 2-Cl,4-OCH₃—C₆H₃ | H | (COOH)₂ | — | 2 | — |
| 2,4-(Cl)₂—C₆H₃ | CH₃ | HNO₃ | 0 | — | — |
| 2,4-(Cl)₂—C₆H₃ | C₂H₅ | HNO₃ | — | 0 | 0 |
| 2,4-(Cl)₂—C₆H₃ | nC₃H₇ | HNO₃ | — | 0 | 0 |
| 2,4-(Cl)₂—C₆H₃ | nC₄H₉ | 1½(COOH)₂ | — | 2 | — |
| 2,4-(Cl)₂—C₆H₃ | nC₅H₁₁ | HNO₃ | — | 0 | 0 |
| 2,4-(Cl)₂—C₆H₃ | nC₆H₁₃ | HNO₃ | 0 | — | — |
| 2,4-(Cl)₂—C₆H₃ | nC₇H₁₅ | HNO₃ | — | 2 | — |
| 2,4-(Cl)₂—C₆H₃ | nC₈H₁₇ | HNO₃ | 0 | — | — |

A.1 Prophylactic action against *Erysiphe polyphaga* on cucumber upon foliar treatment.

Young cucumber plants in the one-leaf stage were sprayed with an aqueous solution containing 500, 250 or 125 ppm of (I-a) while controls were kept untreated. Artificial infection with spores of *Erysiphe polyphaga* was carried out by slightly rubbing the plants with a heavily infected leaf on the 4th., 6th. or 8th. day after treatment. At the 18th. and 34th. day after treatment, the percentage of leaf surface attacked by the fungus were determined separately for the infected leaves and for the newly developed leaves. The results given in Table I.1 are mean values for 5 plants and expressed in percent attack as compared to untreated.

TABLE I.1

Prophylactic activity of (I-a) against *Erysiphe polyphaga* on cucumber upon foliar treatment:

| Date of evaluation | 18 days after treatment | | | | | | 34 days after treatment | | | | | |
|---|---|---|---|---|---|---|---|---|---|---|---|---|
| Infected at stated day after treatment | 4 | | 6 | | 8 | | 4 | | 6 | | 8 | |
| Infected leaves (a) or newly developed leaves (b) | a | b | a | b | a | b | a | b | a | b | a | b |
| Concentr. of (I-a) in spray solution | | | | | | | | | | | | |
| Untreated | 100 | 100 | 100 | 100 | 100 | 100 | 100 | 100 | 100 | 100 | 100 | 100 |
| 500 ppm | 0 | 0 | 0 | 0 | 0 | 0 | 0 | 0 | 0 | 0 | 0 | 0 |
| 250 ppm | 0 | 0 | 0 | 0 | 0 | 0 | 0 | 0 | 0 | 0 | 0 | 0 |
| 125 ppm | 0 | 0 | 0 | 0 | 0 | 0 | 0 | 0 | 0 | 0 | 0 | 0 |

B. Prophylactic action against *Erysiphe graminis* on barely upon soil treatment.

Barley plants were treated by watering with 100 ml. per plant of an aqueous solution containing 1.000, 100 or 10 ppm of (I-a). Controls received the same volume of the solution containing no (I-a). Natural infection, which normally occurs when the plants are held in the glass-house in the vicinity of infected plants, was evaluated 16 days after treatment by counting the number of spots on the leaves. Per object 5 plants were used and the results in Table II are mean values expressed in percent attack as compared to the controls.

TABLE II:

Prophylactic action of (I-a) against *Erysiphe graminis* on barley upon soil treatment.

| Dose in mg. (I-a) per plant | % attack versus control |
|---|---|
| Control | 100 |
| 100 mg | 0 |
| 10 mg | 0 |
| 1 mg | 53 |

C. Curative action against *Erysiphe graminis* on barley upon foliar treatment.

Barely plants attacked by *Erysiphe graminis* were sprayed with an aqueous solution containing (I-a) at the indicated concentration. On the 16th. day after treatment the number of spots per plant was determined. Per object 5 plants were used and the results given in Table III are mean values expressed in percent attack as compared to control.

TABLE III:

Curative action of (I-a) against *Erysiphe graminis* on barley upon foliar treatment.

| Concentration of (I-a) in the spray-solution | % attack compared to control |
|---|---|
| 0 | 100 |
| 1.000 ppm | 0 |
| 100 ppm | 1.5 |
| 10 ppm | 25 |

D. Prophylactic action of (I-a) against *Podosphaera leuchortricha* on apple seedlings upon spraying.

Apple seedlings, one year old, were sprayed with an aqueous solution containing (I-a) at the indicated concentration. The plants were artificially infected as described in test "A" with spores of *Podosphaera leuchotricha* 1 day after treatment and incubated for 36 hours. The degree o fungal attack was evaluated 25 days after treatment by counting the number of spots. Per object 2 plants were used and the results given in Table IV are mean values expressed in percent attack as compared to control.

TABLE IV:

Prophylactic action of (I-a) against *Podosphaera leucotricha* on apple seedlings upon spraying.

| Concentration of (I-a) in spraying solution | % attack compared to control |
|---|---|
| 0 | 100 |
| 100 ppm | 0 |
| 10 ppm | 6 |

E. Activity against *Thielaviopsis sp.*

Slides of potato and leek, 5 mm. thick, were dipped in an aqueous test solution, containing (I-a) at the stated concentration. After dipping, the slides were placed on filter paper in a large plastic tray and the tray was covered with glass. Artificial infection was carried out at the day of treatment by spraying the slides with a concentrated suspension of spores of Thielaviopsis sp. and the slides were incubated at room temperature.

Fungal growth on the slides was evaluated 6 days after treatment by estimating the surface attacked by the fungus. The results given in Table V are expressed in percent attack as compared to the control.

TABLE V:

Activity of (I-a) against *Thielaviopsis sp.*

| Concentration of (I-a) in the test-solution in ppm | % attack compared to control | |
|---|---|---|
| | Potato | Leek |
| 0 | 100 | 100 |
| 1000 | 0 | 0 |
| 100 | 0 | 0 |
| 10 | 0 | 42.8 |
| 1 | 11 | 100 |

The compounds of formula (I) are also very active against a wide variety of fungi which are pathogenic to human beings and animals. For example they are active against fungi such as *Microsporum canis, Trichlophyton mentagrophytes, Trichophyton rubrum, Aspergillus fumigatus, Phialophora verucosa, Cryptococcus neoformans, Candida albicans, Candida tropicalis*, etc.. The excellent activity against *Candida albicans* is more clearly demonstrated by the results obtained in the following experiments.

F. Activity of (I-a) against crop candidosis in turkeys.

Young turkeys (14 days old) were artificially infected by gavage into the crop of a suspension containing $4.10^6$ C.F.U. (colony forming units) of *Candida albicans*.

After the infection the animals received either their normal diet (control group) or a medicated food containing 125 ppm of (I-a). Two weeks thereafter all turkeys were sacrificed, cultures were made of the crop, and the number of candida colonies per gram of crop were counted.

The results are summarized in Table VI.

TABLE VI:

Number of colonies of *Candida albicans* per gram of crop in turkeys treated with (I-a) – (125 ppm) placebo.

| Treatment | Number of the animal | Number of *Candida* colonies per gram crop |
|---|---|---|
| Controls | 1 | 3,520,000 |
| | 2 | 848,700 |
| | 3 | 3,132,000 |
| | 4 | 1,909,000 |
| (I-a) (125 ppm) | 1 | 0 |
| | 2 | 247,200 |
| | 3 | 6,742 |

As is shown by the results in Table VI, (I-a) at the 125 ppm level is highly effective against crop candidosis as compared to the corresponding controls.

G. Activity of (I-a) against vaginal candidosis in rats.

Female rats of 100 g. body weight were ovariectomized and hysterectomized. About three weeks thereafter all animals received a weekly subcutaneous injection of 100 mg. oestradiol undecylate and were infected intravaginally with a suspension containing $8.10^5$ C.F.U. of *Candida albicans*.

Groups of four rats were then orally treated for 14 consecutive days with either solvent (PEG 200) or (I-a). The administered dose of the compound was 40 mg/kg orally. Vaginal smears were taken from all animals at the end of the treatment period (i.e. 14 days), cultivated on Sabouraud agar medium containing Penicillin (20 I.U./ml) and Streptomycin (40 μg/ml), and the number of Candida colonies were counted thereafter.

Table VII summarizes the results obtained with (I-a) against vaginal candidosis in rats.

TABLE VII:

| | Number of animals per culture score | | | | | | |
|---|---|---|---|---|---|---|---|
| | Number of | Day after | Culture score[a] | | | | |
| Treatment | animals | treatment | 0 | 1 | 2 | 3 | 4 |
| Controls (PEG 200) | 4 | 14 | 0 | 0 | 0 | 1 | 3 |
| (I-a) (40 mg/kg orally) | 4 | 14 | 3 | 1 | 0 | 0 | 0 |

[a] culture score:
0 = no growth
1 = 1-25 colonies
2 = 26-100 colonies
3 = >100 colonies
4 = innumerable colonies As is apparent from the results in Table VII, (I-a) is a very potent agent against vaginal candidosis in rats.

H. Activity of (I-a) against systemic candidosis in guinea pigs.

Adult male guinea pigs were intravenously infected with *Candida albicans*, which induces a general systemic candidosis.

Afterwards groups of 7 guinea pigs were orally treated for 14 consecutive days with either solvent (PEG 200) or (I-a). The dose used was 40 mg/kg. body weight.

Four days after the last treatment days, all animals were sacrificed, the kidneys removed, cultivated on Sabouraud agar medium containing Penicillin (20 I.U./ml) and Streptomycin (40 μg/ml) and the number of isolated *Candida albicans* colonies per gram kidney were counted. Table VIII shows the detailed results obtained with (I-a) against systemic deep mycosis in guinea pigs.

TABLE VIII:

| Treatment | Number of the animal | Number of *Candida* colonies per gram kidney |
|---|---|---|
| Controls (PEG 200) | 1 | 182 |
| | 2 | 2,838 |
| | 3 | 25,220 |
| | 4 | 385 |
| | 5 | 19,800 |
| | 6 | 113 |
| | 7 | 345 |
| (I-a) (40 mg/kg orally) | 1 | 0 |
| | 2 | 18 |
| | 3 | 0 |
| | 4 | 0 |
| | 5 | 0 |
| | 6 | 53 |
| | 7 | 0 |

From the results in Table VIII is may be concluded that (I-a) is an extremely potent agent against deep mycosis in guinea pigs.

Apart from their antimicrobial effects, the compounds of formula (I) possess valuable plant growth regulating properties. Depending on different factors such as the species of the plants under treatment and the dose of active ingredient administered, the observed effect may be growth stimulation as well as growth inhibition. As such the compounds of this invention are useful as plant growth regulators. More particularly they may be used as plant growth inhibitors or retardants, especially as inhibitors of sucker growth, e.g., on tobacco plants. Under certain circumstances they may however also be used as plant growth stimulators.

The plant growth regulating properties of the compounds of formula (I), which are naturally intended to be within the scope of this invention, are more clearly illustrated by the results obtained in the following experiments, wherein the compound (I-a) was used as a representative member of the compounds of this invention. The results obtained with (I-a) are not given for the purpose of limiting the invention thereto but only in order to exemplify the useful plant growth regulating properties of all the compounds within the scope of formula (I).

I. Growth regulating effect on tomato plants upon soil treatment.

Young tomato plants 3.5 to 4 cm. high were planted in separate pots. Each pot was watered with a test solution containing the indicated amount of (I-a). Growth was evaluated by determining the length and the weight of the plants 28 days after treatment.

The results given in Table IX are mean values of five plants expressed in percent as compared to the control plants.

TABLE IX:

| Growth regulating effect of (I-a) on tomato plants upon soil treatment. | | |
|---|---|---|
| Dose of (I-a) in mg/plant | Length of plants in % compared to control | Weight of plants in % compared to control |
| none | 100 | 100 |
| 10 | 114 | 118 |
| 1 | 127 | 134 |
| 0.1 | 122 | 116 |

J. Growth regulating effect on barley upon foliar treatment.

Young barley plants in the 3-4 leaf-stage were sprayed with a test solution containing (I-a) in the indicated concentration. The effect on the growth of the plants is evaluated 24 days after treatment by determining the weight of the plants. The results given in Table X are mean values of ten plants expressed in percent as compared to the controls.

TABLE X:

| Growth regulating effect of (I-a) on barley upon foliar teatment. | |
|---|---|
| Conc. of (I-a) in test solution in ppm | Average weight of plants in percent of control |
| none | 100 |
| 125 | 126 |
| 60 | 116 |

K. Sucker growth control on tobacco plants.

Tobacco plants, var. "Xanthi" were raised in the greenhouse and topped at the early button stage.

After 5 days, foliar spray treatment with an aqueous suspension of compound (I-a) at rates equivalent of 3 and 1.5 kg a.i./ha was carried out.

Each treatment was replicated 3 times. 12 Days after application, the subsequent sucker growth was assessed in comparison to the topped and untreated check plants.

The recorded reductions of sucker growth were 100% at the 3.0 kg/ha rate and 90% at 1.5 kg/ha.

L. Growth inhibition on soybean plants.

Soybean plants, var. "Hark" were grown in pots in the growth chamber at 23° C, 20 000 Lux and a daylength of 14 hours. After the 3rd. trifoliate leaf had unfolded, the plants were sprayed with an aqueous suspension of compound (I-a) at concentrations of 1000, 500, 100 and 50 ppm active ingredient.

The % growth inhibition of the treated plants in comparison to the check was assessed after 14 days. The following results were obtained:

| | Treatment | % growth inhibition |
|---|---|---|
| (I-a) | 1000 ppm a.i. | 70% |
| | 500 ppm a.i. | 40% |
| | 100 ppm a.i. | 25% |

| Treatment | % growth inhibition |
|---|---|
| 50 ppm a.i. | 0% |
| check | 0% |

At the concentration of 1000 ppm, a more intensive green colour of the foliage was observed.

In view of the aforementioned antifungal, antibacterial and growth-regulating activities this invention provides valuable compositions comprising the subject ketals (I) or the acid addition salts thereof as the active ingredient in a solvent or a solid, semi-solid or liquid diluent or carrier, and, in addition, it provides an effective method of combatting fungus or bacterial growth by use of an effective antifungal or antibacterial amount of such ketals (I) or salts thereof. The subject compounds can be used in suitable solvents or diluents, in the form of emulsions, suspensions, dispersions or ointments, on suitable solid or semi-solid carrier substances, in ordinary or synthetic soaps, detergents or dispersion media, if desired, together with other compounds having arachnicidal, insecticidal, ovicidal, fungicidal and/or bactericidal effects, or together with inactive additives.

Solid carrier substances which are suitable for the preparation of compositions in powder form include various inert, porous and pulverous distributing agents of inorganic or organic nature, such as, for example, tricalcium phosphate, calcium carbonate, in the form of prepared chalk or ground limestone, kaolin, bole, bentonite, talcum, kieselguhr and boric acid; powdered cork, sawdust, and other fine pulverous materials of vegetable origin are also suitable carrier substances.

The active ingredient is mixed with these carrier substances, for example, by being ground therewith; alternatively, the inert carrier substance is impregnated with a solution of the active component in a readily volatile solvent and the solvent is thereafter eliminated by heating or by filtering with suction at reduced pressure. By adding wetting and/or dispersing agents, such pulverous preparations can also be made readily wettable with water, so that suspensions are obtained.

Inert solvents used for the production of liquid preparations should preferably not be readily inflammable and should be as far as possible odorless and as far as possible non-toxic to warm-blooded animals or plants in the relevant surroundings. Solvents suitable for this purpose are high-boiling oils, for example, of vegetable origin, and lower-boiling solvents with a flash point of at least 30° C., such as, for example, polyethylene glycol, isopropanol, dimethylsulfoxide, hydrogenated naphthalenes and alkylated naphthalenes. It is, of course, also possible to use mixtures of solvents. Solutions can be prepared in the usual way, if necessary, with assistance of solution promotors. Other liquid forms which can be used consist of emulsions or suspensions of the active compound in water or suitable inert solvents, or also concentrates for preparing such emulsions, which can be directly adjusted to the required concentration. For this purpose, the active ingredient is, for example, mixed with a dispersing or emulsifying agent. The active component can also be dissolved or dispersed in a suitable inert solvent and mixed simultaneously or subsequently with a dispersing or emulsifying agent.

It is also possible to use semi-solid carrier substances of a cream ointment, paste or waxlike nature, into which the active component can be incorporated, if necessary, with the aid of solution promotors and/or emulsifiers. Vaseline and other cream bases are examples of semi-solid carrier substances.

Furthermore, it is possible for the active component to be used in the form of aerosols. For this purpose, the active component is dissolved or dispersed, if necessary, with the aid of suitable inert solvents as carrier liquids, such as difluorodichloromethane, which at atmospheric pressure boils at a temperature lower than room temperature, or in other volatile solvents. In this way, solutions under pressure are obtained which, when sprayed, yield aerosols which are particularly suitable for controlling or combatting fungi and bacteria, e.g., in closed chambers and storage rooms, and for application to vegetation for eradicating or for preventing infections by fungi or bacteria.

The subject compounds and compositions thereof can be applied by conventional methods. For example, a fungus or bacterial growth or a material to be treated or to be protected against attack by fungus or bacterium can be treated with the subject compounds and the compositions thereof by dusting, sprinkling, spraying, brushing, dipping, smearing, impregnating or other suitable means.

When the subject compounds are employed in combination with suitable carriers, e.g., in solution, suspension, dust, power, ointment, emulsion, and the like forms, a high activity over a very high range of dilution is observed. For example, concentrations of the active ingredient ranging from 0.1 - 10 percent by weight, based on the weight of composition employed, have been found effective in combatting fungi or bacteria, Of course, higher concentrations may also be employed as warranted by the particular situation.

The following examples are intended to illustrate, but not to limit, the scope of the present invention. Unless otherwise stated, all parts are by weight.

EXAMPLE I

A. To a stirred solution of 2.3 parts of sodium in 120 parts of methanol are added 6.9 parts of 1H-1,2,4-triazole in 150 parts of dimethylformamide. The methanol is removed at normal pressure till the internal temperature of 130° C. Then 25 parts of 2-(bromomethyl)-2-(2,4-dichlorophenyl)-1,3-dioxolane are added. The reaction mixture is stirred and refluxed for 3 hours. It is allowed to cool to room temperature and poured onto water. The precipitated product is filtered off and crystallized from diisopropylether (activated charcoal), yielding 12 parts of 1-[2-(2,4-dichlorophenyl)-1,3-dioxolan-2-ylmethyl]-1H-1,2,4-triazole; mp. 109.9° C.

B. 6 Parts of 1-[2-(2,4-dichlorophenyl)-1,3-dioxolan-2-ylmethyl]-1H-1,2,4-triazole are converted into the nitrate salt in 2,2'-oxybispropane. After cooling, the salt is filtered off and crystallized twice from 2-propanone, yielding 3 parts of 1-[2-(2,4-dichlorophenyl)-1,3-dioxolan-2-ylmethyl]-1H-1,2,4-triazole nitrate; mp. 172.7° C.

C. 6 Parts of 1-[2-(2,4-dichlorophenyl)-1,3-dioxolan-2-ylmethyl]-1H-1,2,4-triazole are converted into the sulfate salt in 2,2'-oxybispropane. The formed sulfate salt is filtered off and crystallized from 2-propanol. The product is filtered off and recrystallized from ethanol (activated charcoal), yielding, after drying, 6 parts of 1-[2-(2,4-dichlorophenyl)-1,3-dioxolan-2-ylmethyl]-1H-1,2,4-triazole sulfate; mp. 207.1° C.

EXAMPLE II

To a stirred solution of 2.3 parts of sodium in 80 parts of methanol are added 6.9 parts of 1H-1,2,4-triazole and 2 parts of sodium iodide in 100 parts of N,N-dimethylformamide. The methanol is removed at normal pressure till the internal temperature of 130° C. Then 34.4 parts of 2-(bromomethyl)-2-(2,4-dichlorophenyl)-4-methyl-1,3-dioxolane are added and the whole is stirred and refluxed for 3 hours. The reaction mixture is poured onto water and the product is extracted twice with diisopropylether. The extract is washed with water and an excess of concentrated nitric acid solution is added. The crude nitrate salt is filtered off and crystallized from a mixture of 2-propanol and diisopropylether, yielding 15 parts of 1-[2-(2,4-dichlorophenyl)-4-methyl-1,3-dioxolan-2-ylmethyl]-1H-1,2,4-triazole nitrate; mp. 137.8° C.

EXAMPLE III

To a stirred sodium methoxide solution, prepared starting from 2.8 parts of sodium in 48 parts of methanol, are added 8.3 parts of 1H-1,2,4-triazole. After stirring for 30 minutes at room temperature, 135 parts of N,N-dimethylformamide are added and the methanol is evaporated. Then there is added a mixture of 24.3 parts of 2-(bromomethyl)-2-phenyl-1,3-dioxolane and 3 parts of potassium iodide, and the whole is stirred and refluxed for 3 hours. The reaction mixture is cooled to room temperature and poured onto water. Upon scratching, the product is precipitated. It is sucked off, washed with water, dried and crystalized from a mixture of ethanol and 2,2'-oxybispropane (1 : 5 by volume), yielding 10.9 parts (43.7%) of 1-(2-phenyl-1,3-dioxolan-2-ylmethyl)-1H-1,2,4-triazole; mp. 127.3° C.

EXAMPLE IV

To a stirred sodium methoxide solution, prepared starting from 2.8 parts of sodium in 48 parts of methanol, are added 8.3 parts of 1H-1,2,4-triazole. After stirring for 30 minutes at room temperature, 135 parts of N,N-dimethylformamide are added and the methanol is evaporated. Then there is added a mixture of 28.8 parts of 2-(bromomethyl)-2-(4-nitrophenyl)-1,3-dioxolane and 3 hours. The reaction mixture is cooled to room temperature and poured onto water. Upon scratching, the product is precipitated. It is sucked off, washed with water, dried and crystallized from a mixture of ethanol and 2,2'-oxybispropane (1 : 10 by volume), yielding 7.3 parts (26.5%) of 1-[2-(4-nitrophenyl)-1,3-dioxolan-2-ylmethyl]-1H-1,2,4-triazole; mp. 160.1° C.

EXAMPLE V

To a stirred sodium methoxide solution, prepared starting from 2.8 parts of sodium in 48 parts of methanol, are added 8.3 parts of 1H-1,2,4-triazole. After stirring for 30 minutes at room temperature, 135 parts of N,N-dimethylformamide are added, and the methanol is evaporated. Then there is added a mixture of 27.75 parts of 2-(bromomethyl)-2-(3-chlorophenyl)-1,3-dioxolane and 3 parts of potassium iodide and the whole is stirred and refluxed for 3 hours. The reaction mixture is cooled to room temperature and poured onto water. Upon scratching, the product is precipitated. It is sucked off, washed with water, dried and crystallized from a mixture of ethanol and 2,2'-oxybispropane (1 : 5 by volume), yielding 14.6 parts (55%) of 1-[2-(3-chlorophenyl)-1,3-dioxolan-2-yl-methyl]-1H-1,2,4-triazole; mp. 113.9° C.

EXAMPLE VI

To a stirred sodium methoxide solution, prepared starting from 2.8 parts of sodium in 56 parts of methanol, is added a mixture of 8.3 parts of 1H-1,2,4-triazole and 135 parts of N,N-dimethylformamide. The methanol is removed at normal pressure till an internal temperature of 130° C. is reached. Then there is added a mixture of 27.8 parts of 2-(bromomethyl)-2-(2-chlorophenyl)-1,3-dioxolane and 3 parts of potassium iodide. The whole is stirred and refluxed for 6 hours. The reaction mixture is allowed to cool to room temperature, poured onto water and the product is extracted three times with 1,1'-oxybisethane. The combined extracts are washed twice with water, dried, filtered and evaporated. The residue is converted into the ethanedioate salt in 4-methyl-2-pentanone. The salt is filtered off and crystallized from 4-methyl-2-pentanone, yielding 16 parts of 1-[2-(2-chlorophenyl)-1,3-dioxolan-2-ylmethyl]-1H-1,2,4-triazole ethanedioate; mp. 156.5° C.

EXAMPLE VII

To a stirred sodium methoxide solution, prepared starting from 2.8 parts of sodium in 48 parts of methanol, is added a mixture of 8.3 parts of 1H-1,2,4-triazole and 135 parts of N,N-dimethylformamide. The methanol is removed at normal pressure till an internal temperature of 130° C. is reached. Then there is added a mixture of 32.2 parts of 2-(bromomethyl)-2-(4-bromophenyl)-1,3-dioxolane and 3 parts of potassium iodide, and the whole is stirred and refluxed for 6 hours. The reaction mixture is allowed to cool to room temperature and poured onto water. The precipitated product is filtered off and crystallized from a mixture of N,N-dimethylformamide and water, yielding 22.4 parts of 1-[2-(4-bromophenyl)-1,3-dioxolan-2-ylmethyl]-1H-1,2,4-triazole; mp. 135.9° C.

EXAMPLE VIII

To a stirred sodium methoxide solution, prepared starting from 2.8 parts of sodium in 56 parts of methanol, are added successively 8.2 parts of 1H-1,2,4-triazole and 135 parts of N,N-dimethylformamide. The methanol is distilled off at normal pressure till an internal temperature of 130° C. Then there are added successively 32.2 parts of 2-(bromomethyl)-2-(2-bromophenyl)-1,3-dioxolane and 3 parts of potassium iodide. The whole is stirred and refluxed overnight. The reaction mixture is allowed to cool to room temperature and the product is extracted twice with 1,1'-oxybisethane. The combined extracts are washed with water and an excess of ethanedioic acid dihydrate is added. The formed ethanedioate salt is filtered off and crystallized from 4-methyl-2-pentanone, yielding 13.5 parts of 1-[2-(2-bromophenyl)-1,3-dioxolan-2-ylmethyl]-1H-1,2,4-triazole ethanedioate; mp. 172.1° C.

EXAMPLE IX

To a stirred sodium methoxide solution, prepared starting from 2.3 parts of sodium in 48 parts of methanol, are added 6.9 parts of 1H-1,2,4-triazole. After stirring for 30 minutes at room temperature, there are added 135 parts of N,N-dimethylformamide and the methanol is distilled off at normal pressure till an internal temperature of $\leq$ 130° C. Then there are added 21 parts of 2-(bromomethyl)-2-(m-methoxyphenyl)-1,3- dioxolane and 3 parts of potassium iodide and the whole is stirred and refluxed overnight. The reaction mixture is cooled to room temperature and poured onto water. Upon scratching, the product is precipitated. It is sucked off, washed with water and converted into the ethanedioate salt in 4-methyl-2-pentanone. The salt is filtered off and crystallized from a mixture of 2-propanone and 2,2'-oxybispropane (1 : 1 by volume), yielding 14.2 parts (52%) of 1-[2-(3-methoxyphenyl)-1,3-dioxolan-2-ylmethyl]-1H-1,2,4-triazole ethanedioate; mp. 155.6° C.

EXAMPLE X

To a stirred sodium methoxide solution, prepared starting from 2.8 parts of sodium in 48 parts of methanol, are added 8.3 parts of 1H-1,2,4-triazole. After stirring for 30 minutes at room temperature, 135 parts of N,N-dimethylformamide are added. The methanol is distilled off at normal pressure till an internal temperature of ≦130° C.. Then there are added successively 3 parts of potassium iodide and 26.5 parts of 2-(bromomethyl)-2-o-tolyl-1,3-dioxolane and the whole is stirred and refluxed overnight. After cooling to room temperature, the reaction mixture is poured onto water. Upon scratching, the product is recipitated. It is filtered off, washed with water and dissolved in 4-methyl-2-pentanone. An excess of ethanedioic acid dihydrate is added to the solution. The formed salt is filtered off and crystallized from a mixture of 2-propanone and 2,2'-oxybispropane (2 : 1 by volume), yielding 13.7 parts (41%) of 1-[2-(2-methylphenyl)-1,3-dioxolan-2-ylmethyl]-1H-1,2,4-triazole ethanedioate; mp. 177.1° C.

EXAMPLE XI

To a stirred sodium methoxide solution, prepared starting from 2.8 parts of sodium in 48 parts of methanol, are added 8.3 parts of 1H-1,2,4-triazole. After stirring for 30 minutes at room temperature, 135 parts of N,N-dimethylformamide are added. The methanol is distilled off at normal pressure till internal temperature of 130° C.. Then there are added successively 3 parts of potassium iodide and 26.1 parts of 2-(bromomethyl)-2-(4-fluorophenyl)-1,3-dioxolane and the whole is stirred and refluxed overnight. After cooling to room temperature, the reaction mixture is poured onto water. The formed precipitate is filtered off, washed with water and converted into the ethanedioate salt in 4-methyl-2-pentanone. The salt is filtered off and crystallized from a mixture of 2-propanone and 2,2'-oxybispropane (1 : 1 by volume), yielding 16.2 parts (48%) of 1-[2-(4-fluorophenyl)-1,3-dioxolan-2-ylmethyl]-1H-1,2,4-triazole ethanedioate; mp. 185.5° C..

EXAMPLE XII

To a stirred sodium methoxide solution, prepared starting from 2.8 parts of sodium in 48 parts of methanol, are added 8.3 parts of 1H-1,2,4-triazole. After stirring for 30 minutes at room temperature, 135 parts of N,N-dimethylformamide are added. The methanol is distilled off at normal pressure till internal temperature of 130° C.. Then there are added successively 25.7 parts of 2-(bromomethyl)-2-(4-methylphenyl)-1,3-dioxolane and 3 parts of potassium iodide, and the whole is stirred and refluxed overnight. After cooling to room temperature, the reaction mixture is poured onto water. The precipitated product is filtered off, washed with water and converted into the ethanedioate salt in 4-methyl-2-pentanone. The salt is filtered off and crystallized from a mixture of 2-propanone and 2,2'-oxybispropane (1 : 1 by volume), yielding 8.6 parts (26%) of 1-[2-(4-methylphenyl)-1,3-dioxolan-2-ylmethyl]-1H-1,2,4-triazole ethanedioate; mp. 151.2° C..

EXAMPLE XIII

To a stirred sodium methoxide solution, prepared starting from 2.8 parts of sodium in 56 parts of methanol, are added 8.2 parts of 1H-1,2,4-triazole. After the addition of 135 parts of N,N-dimethylformamide, the methanol is distilled off at normal pressure till internal temperature of 130° C.. Then there are added successively 26.4 parts of 2-(bromomethyl)-2-(4-chlorophenyl)-1,3-dioxolane and 3 parts of potassium iodide. The whole is stirred and refluxed overnight. The reaction mixture is poured onto water and the recipitated product is filtered off. It is crystallized from methylbenzene, filtered off again and converted into the ethanedioate salt in 4-methyl-2-pentanone and 2,2'-oxybispropane. The salt is filtered off and crystallized from 4-methyl-2-pentanone, yielding 15.7 parts of 1-[2-(4-chlorophenyl)-1,3-dioxolan-2-ylmethyl]-1H-1,2,4-triazole ethanedioate hydrate; mp. 169.1° C..

EXAMPLE XIV

To a stirred sodium methoxide solution, prepared starting from 2.8 parts of sodium in 40 parts of methanol, are added 8.2 parts of 1H-1,2,4-triazole. After the addition of 135 parts of N,N-dimethylformamide, the methanol is removed in vacuo till an internal temperature of 130° C. is reached. Then there are added successively 27.3 parts of 2-(bromomethyl)-2-(4-methoxyphenyl)-1,3-dioxolane and 3 parts of potassium iodide, and the whole is stirred and refluxed overnight. The reaction mixture is allowed to cool to room temperature and poured onto crushed ice. The precipitated product is filtered off and converted into the ethanedioate salt in 4-methyl-2-pentanone. The salt is filtered off and crystallized from a mixture of ethanol and 2,2'-oxybispropane, yielding 10 parts of 1-[2-(4-methoxyphenyl)-1,3-dioxolan-2-ylmethyl]-1H-1,2,4-triazole ethanedioate; mp. 187.1° C.

EXAMPLE XV

To a stirred solution of 74.4 parts of 2-bromo-1-(2-naphthalenyl)-1-ethanone in 240 parts of a butanol are added successively 3 parts of 4-methylbenzenesulfonic acid and 270 parts of benzene. Then there are added dropwise 28 parts of 1,2-ethanediol. Upon completion, stirring is continued overnight at reflux temperature. The reaction mixture is evaporated. The residue is dissolved in 2,2'-oxybispropane and the solution is stirred with a diluted sodium hydroxide solution. The layers are separated and the aqueous phase is extracted with 2,2'-oxybispropane. The extra ct is neutralized with water, dried, filtered and evaporated. The oily residue is crystallized from methanol. The product is filtered off and recrystallized from methanol, yielding 41 parts of 2-(bromomethyl)-2-(2-naphthalenyl)-1,3-dioxolane; mp. 64° C.

To a stirred sodium methoxide solution, prepared starting from 2.3 parts of sodium in 48 parts of methanol, are added 6.9 parts of 1H-1,2,4-triazole. After stirring for 30 minutes at room temperature, 135 parts of N,N-dimethylformamide are added. The methanol is distilled off at normal pressure till internal temperature of 130° C.. Then there are added successively 3 parts of potassium iodide and 14.6 parts of 2-(bromomethyl)-2-

(2-naphthalenyl)-1,3-dioxolane, and the whole is stirred and refluxed overnight. The reaction mixture is cooled to room temperature and poured onto water. The precipitated product is filtered off, washed thoroughly with water and dissolved in 4-methyl-2-pentanone. An excess of ethanedioic acid dihydrate is added. The formed ethanedioate salt is filtered off and crystallized from a mixture of 2-propanone and 2,2'-oxybispropane (2 : 1 by volume), yielding 9.5 parts (51%) of 1-[2-(2-naphthalenyl)-1,3-dioxolan-2-ylmethyl]-1H-1,2,4-triazole ethanedioate; mp. 175° C..

EXAMPLE XVI

To a stirred sodium methoxide solution, prepated starting from 2.3 parts of sodium in 48 parts of methanol, are added 6.9 parts of 1H-1,2,4-triazole and stirring is continued for 30 minutes at room temperature. After the addition of 135 parts of N,N-dimethylformamide, the methanol is removed at normal pressure till an internal temperature of 130° C. is reached. Then there are added 23.4 parts of 2-(bromomethyl)-2-(2,5-dichlorophenyl)-1,3-dioxolane and 3 parts of potassium iodide. The whole is stirred and refluxed for 17 hours. The reaction mixture is cooled to room temperature and poured onto water. The precipitated product is sucked off, washed with water and converted into the ethanedioate salt in 4-methyl-2-pentanone. The salt is filtered off and crystallized from a mixture of 2-propanone and 2,2'-oxybispropane (1 : 2 by volume), yielding 6.1 parts (21%) of 1-[2-(2,5-dichlorophenyl)-1,3-dioxolan-2-ylmethyl]-1H-1,2,4-triazole ethanedioate; mp. 173.7° C..

EXAMPLE XVII

To a stirred solution of 112 parts of 4-(2-bromoacetyl)benzonitrile in 320 parts of butanol are added 5 parts of 4-methylbenzenesulfonic acid and 360 parts of benzene. Then there are added dropwise 46.5 parts of 1,2-ethanediol. Upon completion, stirring is continued for 4 hours at reflux. The reaction mixture is evaporated. The oily residue is crystallized from 2,2'-oxybispropane. The product is filtered off and recrystallized from methanol, yielding 95.12 parts of 4-[2-(bromomethyl)-1,3-dioxolan-2-yl]-benzonitrile; mp. 92.4° C..

To a stirred sodium methoxide solution, prepard starting from 2.3 parts of sodium in 48 parts of methanol, are added 6.9 parts of 1H-1,2,4-triazole and 135 parts of N,N-dimethylformamide. After stirring for one hour at room temperature, the methanol is distilled off at normal pressure till internal temperature of 130° C.. Then there are added successively 3 parts of potassium iodide and 20.1 parts of 4-[2-(bromomethyl)-1,3-dioxolan-2-yl]benzonitrile and the whole is stirred and refluxed overnight. The reaction mixture is cooled to room temperature and poured onto water. The precipitated product is sucked off, washed thoroughly with water and converted into the ethanedioate salt in 4-methyl-2-pentanone. The salt is filtered off and crystallized from a mixture of 2-propanone and 2,2'-oxybispropane (2 : 1 by volume), yielding 13.8 parts (54%) of 4-[2-(1H-1,2,4-triazol-1-ylmethyl)-1,3-dioxolan-2-yl]benzonitrile ethanedioate; mp. 186.3° C..

EXAMPLE XVIII

To a stirred sodium methoxide solution, prepared starting from 2.8 parts of sodium in 48 parts of methanol, are added successively 7.5 parts of 1H-1,2,4-triazole, 3 parts of potassium iodide and 135 parts of N,N-dimethylformamide. The methanol is distilled off at normal pressure till internal temperature of 130° C. Then there are added 31.2 parts of 2-(bromomethyl)-2-(3,4-dichlorophenyl)-1,3-dioxolane and the whole is stirred and refluxed for 6 hours. The reaction mixture is allowed to cool to room temperature and poured onto water. The formed precipitate is sucked off and converted into the ethanedioate salt in 4-methyl-2-pentanone and 2,2'-oxybispropane. The salt is filtered off and crystallized from 4-methyl-2-pentanone. The product is filtered off and recrystallized from 2-propanol, yielding 17.9 parts of 1-[2-(3,4-dichlorophenyl)-1,3-dioxolan-2-ylmethyl]-1H-1,2,4-triazole ethanedioate; mp. 182.2° C..

EXAMPLE XIX

By repeating the procedure of Example I, except that the 2-(bromomethyl)-2-(2,4-dichlorophenyl)-1,3-dioxolane used therein is replaced by an equivalent amount of an appropriate 2-(bromomethyl)-2-aryl-1,3-dioxolane, the following compounds of formula (I) are obtained respectively:

1-[2-(2,4,6-trichlorophenyl)-1,3-dioxolan-2-ylmethyl]-1H-1,2,4-triazole;

1-[2-(2,6-dichlorophenyl)-1,3-dioxolan-2-ylmethyl]-1H-1,2,4-triazole;

1-[2-(2-chloro-4-methylphenyl)-1,3-dioxolan-2-ylmethyl]-1H-1,2,4-triazole; and

EXAMPLE XX

The procedure of Example II may be used to prepare compounds of formula (I) wherein Z is —CH$_2$—CH(CH$_3$)— or —CH(CH$_3$)—CH(CH$_3$)—. Accordingly, by substituting therein an equivalent amount of an appropriate 2-aryl-2-(bromomethyl)-4-methyl-1,3-dioxolane or 2-aryl-2-(bromomethyl)-4,5-dimethyl-1,3-dioxolane, the following compounds are obtained respectively in the form of a nitrate salt:

1-(4-methyl-2-phenyl-1,3-dioxolan-2-ylmethyl)-1H-1,2,4-triazole;

1-[2-(4-chlorophenyl)-4-methyl-1,3-dioxolan-2-ylmethyl]-1H-1,2,4-triazole;

1-[2-(2-chlorophenyl)-4-methyl-1,3-dioxolan-2-ylmethyl]-1H-1,2,4-triazole;

1-[4-methyl-2-(4-methylphenyl)-1,3-dioxolan-2-ylmethyl]-1H-1,2,4-triazole;

1-[2-(4-methoxyphenyl)-4-methyl-1,3-dioxolan-2-ylmethyl]-1H-1,2,4-triazole;

1-4,5-dimethyl-2-(2,4-dichlorophenyl)-1,3-dioxolan-2-ylmethyl]-1H-1,2,4-triazole;

1-(4,5-dimethyl-2-phenyl-1,3-dioxolan-2-ylmethyl)-1H-1,2,4-triazole; and

1-[2-(4-chlorophenyl)-4,5-dimethyl-1,3-dioxolan-2-ylmethyl]-1H-1,2,4-triazole.

EXAMPLE XXI

The procedure set forth in Example I may be utilized to prepare those compounds of formula (I) wherein Z is —CH$_2$—CH$_2$—CH$_2$—. Accordingly, by substituting therein an equivalent quantity of an appropriate 2-aryl-2-(bromomethyl)-1,3-dioxane as starting material, the following are obtained respectively:

1-(2-phenyl-1,3-dioxan-2-ylmethyl)-1H-1,2,4-triazole;

1-[2-(2,4-dichlorophenyl)-1,3-dioxan-2-ylmethyl]-1H-1,2,4-triazole;

1-[2-(4-chlorophenyl)-1,3-dioxan-2-ylmethyl]-1H-1,2,4-triazole;

1-[2-(4-methylphenyl)-1,3-dioxan-2-ylmethyl]-1H-1,2,4-triazole;

1-[2-(4-methoxyphenyl)-1,3-dioxan-2-ylmethyl]-1H-1,2,4-triazole;

1-[2-(2-thienyl)-1,3-dioxan-2-ylmethyl]-1H-1,2,4-triazole; and

1-[2-(2-naphthyl)-1,3-dioxan-2-ylmethyl]-1H-1,2,4-triazole.

EXAMPLE XXII

The compositions according to this invention are employed in those forms which are customarily used for fungus or bacteria control, for example, as suspensions, dusting powders, solutions, ointments and the like. The following will further illustrate the invention, the parts being parts by weight unless otherwise specified:

| (1) SUSPENSION: | |
| --- | --- |
| 1 kg. | 1-[2-(2,4-dichlorophenyl)-1,3-dioxolan-2-yl-methyl]-1H-1,2,4-triazole |
| 2 l. | technical xylene |
| 350 ml. | Surfactant |
| Water | dilute to desired concentration to active ingredient |

The 1-[2(2,4-dichlorophenyl)-1,3-dioxolan-2-ylmethyl]-1H-1,2,4-triazole forms a stable aqueous suspension when dissolved in the xylene and emulsified by means of the surface active agent.

(2) DUSTING POWDER

20 Parts of 1-[2-(2,4-dichlorophenyl)-1,3-dioxolan-2-ylmethyl]-1H-1,2,4-triazole are ground with 360 parts of talcum in a ball mill, then 8 parts of olein are added and grinding is continued, and finally the mixture is mixed with 4 parts of slaked lime. The powder which is formed can be sprayed satisfactorily and has good adhesive power. It can be used for dusting or for plant protection purposes.

(3) SOLUTION

5 Parts of 1-[2-(2,4-dichlorophenyl)-1,3-dioxolan-2-ylmethyl]-1H-1,2,4-triazole are dissolved in 95 parts of alkylated naphthalene and used as a spray for the treatment of fungusinfected subjects or on walls, floors, or other objects to prevent infection by fungi.

(4) OINTMENT

10 Parts of 1-[2-(2,4-dichlorophenyl)-1,3-dioxolan-2-ylmethyl]-1H-1,2,4-triazole are dissolved in a warm, liquefied mixture of 400 parts of polyethylene glycol 400 and 590 parts, of polyethylene glycol 1500. The solution is stirred during cooling, and used as an ointment for treatment against fungi and bacteria.

EXAMPLE XXIII

57 Parts of 1-(5-chloro-2-thienyl)-1-ethanone are dissolved in 220 parts of 1,2-ethanediol at 50° C. While stirring, there are added dropwise, during a 1 hour-period, 64 parts of bromine without external heating. After stirring for 1 hour at room temperature, 4 parts of 4-methylbenzenesulfonic acid and 360 parts of benzene are added. The whole is stirred and refluxed overnight with water-separator. The reaction mixture is evaporated and the residue is taken up in 2,2'-oxybispropane. The resulting solution is washed successively once with a diluted sodium hydroxide solution and three times with water, dried, filtered and evaporated. The residue is distilled, yielding 73.3 parts (64.5%) of 2-(bromomethyl)-2-(5-chloro-2-thienyl)-1,3-dioxolane; bp. 125°–127° C. at 0.1 mm. pressure.

To a stirred sodium methoxide solution, prepared starting from 2.8 parts of sodium in 48 parts of methanol, are added 8.3 parts of 1H-1,2,4-triazole. After stirring for 30 minutes at room temperature, 135 parts of N,N-dimethylformamide are added. The methanol is distilled off at normal pressure till internal temperature of 130° C. Then there are added successively 28.3 parts of 2-(bromomethyl)-2-(5-chloro-2-thienyl)-1,3-dioxolane and 4 parts of potassium iodide. The whole is stirred and refluxed overnight. After cooling to room temperature, the reaction mixture is poured onto water. Upon scratching, the product is precipitated, filtered off and washed with water. The product, dissolved in trichloromethane, is purified by column-chromatography over silicagel, using a mixture of trichloromethane and 5% of methanol as eluent. The pure fractions are collected and the eluent is evaporated. The residue is crystallized from a mixture of 2,2'-oxybispropane and methanol (5 : 1 by volume), yielding 7.1 parts (26%) of 1-[2-(5-chloro-2-thienyl)-1,3-dioxolan-2-yl-methyl]-1H-1,2,4-triazole; mp. 117.4° C.

EXAMPLE XXIV

To a stirred sodium methoxide solution, prepared starting from 2.8 parts of sodium in 48 parts of methanol, are added 8.3 parts of 1H-1,2,4-triazole. After stirring for 30 minutes at room temperature, 135 parts of N,N-dimethylformamide are added. The methanol is distilled off at normal pressure till internal temperature of 130° C. Then there are added successively 3 parts of potassium iodide and 25 parts of 2-(bromomethyl)-2-(2-thienyl)-1,3-dioxolan. The whole is stirred and refluxed overnight. After cooling to room temperature, the reaction mixture is poured onto water. The formed precipitate is sucked off, washed three times with water and converted into the ethanedioate salt in 4-methyl-2-pentanone. The salt is filtered off and crystallized from 2-propanol, yielding 9.8 parts (27.5%) of 1-[2-(2-thienyl)-1,3-dioxolan-2-ylmethyl]-1H-1,2,4-triazole ethanedioate; mp. 144.5° C.

EXAMPLE XXV

To a stirred sodium methoxide solution, prepared starting from 1.6 parts of sodium in 48 parts of methanol, are added 4.9 parts of 1H-1,2,4-triazole. After stirring for 1 hour at room temperature, 135 parts of N,N-dimethylformamide are added. The methanol is distilled off at normal pressure till internal temperature of 130° C. Then there are added successively 17.4 parts of 2-(bromomethyl)-2-(2,3,4-trichlorophenyl)-1,3-dioxolane and 3 parts of potassium iodide. The whole is stirred and refluxed overnight. After cooling to room temperature, the reaction mixture is poured onto water. Upon scratching, the product is precipitated, filtered off and washed with water. The product, dissolved in trichloromethane, is purified by column-chromatography over silicagel, using a mixture of trichloromethane and 5% of methanol as eluent. The pure fractions are collected and the eluent is evaporated. The residue is crystallized from a mixture of 2,2'-oxybispropane and methanol (9 : 1 by volume), yielding 9.3 parts (55.5%) of 1-[2-(2,3,4-trichlorophenyl)-1,3-dioxolan-2-ylmethyl]-1H-1,2,4-triazole; mp. 181.4° C.

EXAMPLE XXVI

To a stirred sodium methoxide solution, prepared starting from 2.3 parts of sodium in 48 parts of methanol, are added 6.9 parts of 1H-1,2,4-triazole. After stirring for 30 minutes at room temperature, 135 parts of N,N-dimethylformamide are added. The methanol is distilled off at normal pressure till internal temperature of 130° C. Then there are added successively 3 parts of potassium iodide and 16.4 parts of 2-(bromomethyl)-2-(o-methoxyphenyl)-1,3-dioxolane. The whole is stirred and refluxed for 18 hours. After cooling to room temperature, the reaction mixture is poured onto water and the resulting solution is extracted three times with trichloromethane. The combined extracts are washed four times with water, dried, filtered and evaporated. The residue is purified by column-chromatography over silicagel, using a mixture of trichloromethane and 5% of methanol as eluent. The pure fractions are collected and the eluent is evaporated. The residue is converted into the ethanedioate salt in 4-methyl-2-pentanone. The salt is filtered off and crystallized from a mixture of 2-propanone and 2,2'-oxybispropane (2 : 1 by volume), yielding 5.5 parts (26%) of 1-[2-(2-methoxyphenyl)-1,3-dioxolan-2-ylmethyl]-1H-1,2,4-triazole ethanedioate; mp. 166.4° C.

EXAMPLE XXVII

To a stirred sodium methoxide solution, prepared starting from 2.8 parts of sodium in 48 parts of methanol, are added 8.3 parts of 1H-1,2,4-triazole and 135 parts of N,N-dimethylformamide. After stirring for 1 hour at room temperature, the methanol is distilled off at normal pressure till internal temperature of 130° C. Then there are added successively 3 parts of potassium iodide and 26.5 parts of 2-(bromomethyl)-2-m-tolyl-1,3-dioxolane. The whole is stirred and refluxed overnight. After cooling to room temperature, the reaction mixture is poured onto water. The precipitated product is sucked off, washed with water and crystallized from 2,2'-oxybispropane, yielding 11 parts (50%) of 1-[2-(3-methylphenyl)-1,3-dioxolan-2-ylmethyl]-1H-1,2,4-triazole; mp. 105.4° C.

EXAMPLE XXVIII

To a stirred and hot (50° C.) solution of 64 parts of 1-(3-bromo-4-methylphenyl)-1-ethanone in 160 parts of 1-butanol are added dropwise, during a 1 hour-period, 48 parts of bromine without external heating. After stirring for 1 hour at room temperature, there are added successively 21.7 parts of 1,2-ethanediol, 6 parts of 4-methylbenzenesulfonic acid and 720 parts of benzene. The whole is stirred and refluxed overnight with water-separator. The reaction mixture is evaporated and the residue is taken up in 2,2'-oxybispropane. The resulting solution is washed successively once with a diluted sodium hydroxide solution and three times with water, dried, filtered and evaporated. The residue is distilled, yielding 57 parts (57%) of 2-(bromomethyl)-2-(3-bromo-4-methylphenyl)-1,3-dioxolane; bp. 126°-130° C. at 0.1 mm. pressure.

To a stirred sodium methoxide solution, prepared starting from 1.6 parts of sodium in 48 parts of methanol, are added 4.83 parts of 1H-1,2,4-triazole. After stirring for 30 minutes at room temperature, 135 parts of N,N-dimethylformamide are added. The methanol is distilled off at normal pressure till internal temperature of 130° C. Then there are added successively 19 parts of 2-(bromomethyl)-2-(3-bromo-4-methylphenyl)-1,3-dioxolane and 2 parts of potassium iodide. The whole is stirred and refluxed overnight. The reaction mixture is cooled to room temperature and poured onto water. Upon scratching, the product is precipitated. It is filtered off and washed with water. The crude product, dissolved in trichloromethane, is purified by column-chromatography over silicagel, using a mixture of trichloromethane and 5% of methanol as eluent. The pure fractions are collected and the eluent is evaporated. The residue is crystallized from a mixture of 2,2'-oxybispropane and methanol (9 : 1 by volume), yielding 6.4 parts (35%) of 1-[2-(3-bromo-4-methylphenyl)-1,3-dioxolan-2-ylmethyl]-1H-1,2,4-triazole; mp. 120.7° C.

EXAMPLE XXIX

To a stirred mixture of 78.8 parts of 2-bromo-1-(4-bromo-2-methylphenyl)-1-ethanone and 200 parts of butanol are added 3 parts of 4-methylbenzenesulfonic acid and 225 parts of benzene. Then there are added dropwise 33.5 parts of 1,2-ethanediol. Upon completion, stirring is continued overnight at reflux temperature with water-separator. The reaction mixture is evaporated and the residue is dissolved in 2,2'-oxybispropane. The solution is stirred with 15 parts of a concentrated sodium hydroxide solution. The layers are separated and the aqueous phase is extracted with 2,2'-oxybispropane. The combined organic layers are washed with water (till neutralization), dried, filtered and evaporated. The solid residue is crystallized from methanol, yielding 30.5 parts of 2-(bromomethyl)-2-(4-bromo-2-methylphenyl)-1,3-dioxolane; mp. 86° C.

To a stirred sodium methoxide solution, prepared starting from 2.8 parts of sodium in 56 parts of methanol, are added 8.3 parts of 1H-1,2,4-triazole. The whole is heated and 32 parts of methanol are distilled off. After the addition of 90 parts of N,N-dimethylformamide, the mixture is concentrated to a volume of about 80 parts. Then there are added successively 45 parts of N,N-dimethylformamide, 3.3 parts of potassium iodide and 33.6 parts of 2-(bromomethyl)-2-(4-bromo-2-methylphenyl)-1,3-dioxolane and the whole is stirred and refluxed overnight. After cooling, the reaction mixture is poured onto water, while stirring. The precipitated product is filtered off and purified by column-chromatography over silicagel, using a mixture of trichloromethane and 5% of methanol as eluent. The pure fractions are collected and the eluent is evaporated. The solid residue is crystallized from 2,2'-oxybispropane. The product is filtered off and dried, yielding 5.5 parts of 1-[2-(4-bromo-2-methylphenyl)-1,3-dioxolan-2-ylmethyl]-1H-1,2,4-triazole; mp. 148.1° C.

EXAMPLE XXX

A. A stirred and cooled (0° C) solution of 30 parts of 1-(4-amino-2-methoxyphenyl)ethanone in 360 parts of a concentrated hydrochloric acid solution, 75 parts of water and 30 parts of acetic acid is diazotated with a solution of 17.25 parts of sodium nitrite in 200 parts of water. After stirring for 30 minutes at 0° C, the whole is poured onto a solution of 30 parts of copper (I) chloride in 240 parts of a concentrated hydrochloric acid solution while stirring. The mixture is heated for 1 hour at 60° C. After cooling to room temperature, the product is extracted twice with 2,2'-oxybispropane. The combined extracts are washed successively with water, a diluted sodium hydroxide solution and again twice with water, dried, filtered and evaporated, yielding 28 parts (76%) of 1-(4-chloro-2-methoxyphenyl)-ethanone; mp. 55° C.

B. To a stirred solution of 27.5 parts of 1-(4-chloro-2-methoxyphenyl)ethanone in 160 parts of butanol are added dropwise 24 parts of bromine. After stirring for 1 hour at room temperature, there are added successively 9.3 parts of 1,2-ethanediol, 3 parts of 4-methylbenzenesulfonic acid and 450 parts of benzene. Stirring is continued overnight at reflux temperature with water-separator. The reaction mixture is evaporated and the residue is taken up in benzene. The mixture is washed with a diluted sodium hydroxide solution and three times with water, dried, filtered and evaporated. The residue is crystallized from methanol, yielding 27.6 parts (60%) of 2-(bromomethyl)-2-(4-chloro-2-methoxyphenyl-1,3-dioxolane; mp. 110° C.

EXAMPLE XXXI

Following the procedure of Example XXX-B and using an equivalent amount of an appropriate 1-arylethanone in place of the 1-(4-chloro-2-methoxyphenyl)ethanone used therein, the following dioxolanes are prepared:

2-(bromomethyl)-2-(4-iodophenyl)-1,3-dioxolane; mp. 74° C; and 2-(bromomethyl)-2-(2,4-dibromophenyl)-1,3-dioxolane; mp. 96° C.

EXAMPLE XXXII

To a stirred sodium methoxide solution, prepared starting from 1.15 parts of sodium in 40 parts of methanol, are added 3.5 parts of 1H-1,2,4-triazole. After stirring for 30 minutes at room temperature, 135 parts of N,N-dimethylformamide are added. The methanol is distilled off at normal pressure till internal temperature of 130° C. Then there are added 18.5 parts of 2-(bromomethyl)-2-(4-iodophenyl)-1,3-dioxolane and 2 parts of potassium iodide and the whole is stirred and refluxed for 24 hours. After cooling to room temperature, the reaction mixture is poured onto water. Upon scratching, the product is precipitated. It is filtered off, washed with water and dissolved in trichloromethane. The solution is washed three times with water and 5% by volume of methanol is added. The solution is stirred with silica gel. The latter is filtered off and the filtrate is evaporated. The residue is converted into the ethanedioate salt in 4-methyl-2-pentanone. The salt is filtered off and crystallized from 2-propanone, yielding 4.1 parts (18.3%) of 1-[2-(4-iodophenyl)-1,3-dioxolan-2-yl-methyl]-1H-1,2,4-triazole ethanedioate; mp. 169.8° C.

EXAMPLE XXXIII

Following the procedure of Example XXXII and using equivalent amounts of the appropriate starting materials, the following triazoles and triazole acid addition salts are prepared:

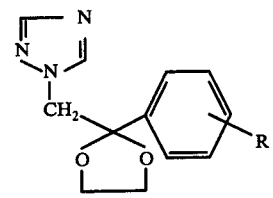

| R | Base or Salt form | Melting Point |
| --- | --- | --- |
| 2-CH₃,4-Cl | base | 147.9° C |
| 3-Br | base | 115.4° C |
| 3,5-(Cl)₂ | (COOH)₂ | 204.4° C |
| 2,3-(Cl)₂ | (COOH)₂ | 188.4° C |
| 3-NO₂ | base | 154.1° C |
| 2-OCH₃,4-Cl | (COOH)₂ | 173.2° C |
| 2,4-(Br)₂ | (COOH)₂ | 190.3° C |
| 2,4,5-(Cl)₃ | (COOH)₂ | 178.4° C |
| 2-Cl,4-OCH₃ | (COOH)₂ | 188.2° C |

EXAMPLE XXXIV

To a stirred mixture of 9.5 parts of 1H-1,2,4-triazole and 225 parts of N,N-dimethylformamide are added portionwise 4.2 parts sodium hydride dispersion 78%. After stirring till foaming is ceased, there are added 16 parts of 2-(bromomethyl)-2-(2,4-dichlorophenyl)-4-propyl-1,3-dioxolane and stirring is continued for 5 hours at reflux temperature. The reaction mixture is cooled and poured onto water. The product is extracted three times with 2,2'-oxybispropane. The combined extracts are washed with water, dried, filtered and evaporated. The residue is purified by column-chromatography over silica gel using a mixture of trichloromethane and 2% of methanol as eluent. The first fraction is collected and the eluent is evaporated. The residue is converted into the nitrate salt in 2,2'-oxybispropane. The salt is filtered off and crystallized from a mixture of 2-propanone and petroleumether, yielding 8.2 parts (45%) of 1-[2-(2,4-dichlorophenyl)-4-propyl-1,3-dioxolan-2-ylmethyl]-1H-1,2,4-triazole nitrate; mp. 132.6° C.

EXAMPLE XXXV

To a stirred sodium methoxide solution, prepared starting from 3.8 parts of sodium in 40 parts of methanol, are added 11.5 parts of 1H-1,2,4-triazole and 225 parts of N,N-dimethylformamide. The methanol is distilled off till internal temperature of 150° C. After the addition of 19 parts of 2-(bromomethyl)-2-(2,4-dichlorophenyl)-4-ethyl-1,3-dioxolane, the whole is stirred and refluxed for 4 hours. The reaction mixture is cooled and poured onto water. The product is extracted three times with 2,2'-oxybispropane. The combined extracts are washed with water, dried, filtered and evaporated. The residue is purified by column-chromatography and evaporated. The residue is purified by column-chromatography over silica gel using a mixture of trichloromethane and 2% of methanol as eluent. The first fraction is collected and the eluent is evaporated. The residue is converted into the nitrate salt in 2,2'-oxybispropane. The salt is filtered off and recrystallized from a mixture of 4-methyl-2-pentanone and 2,2'-oxybispropane, yielding 10.5 parts (49%) of 1-[2-(2,4-dichlorophenyl)-4-ethyl-1,3-dioxolan-2-yl-methyl]-1H-1,2,4-triazole nitrate; mp. 119.8° C.

EXAMPLE XXXVI

Following the procedure of Example XXXV and using equivalent amounts of the appropriate starting materials, the following triazoles and triazole acid addition salts are prepared:

1-[4-butyl-1-(2,4-dichlorophenyl)-1,3-dioxolan-2-ylmethyl]-1H-1,2,4-triazole sesquiethanedioate; mp. 111.6° C;

1-[2-(2,4-dichlorophenyl)-4-pentyl-1,3-dioxolan-2-ylmethyl]-1H-1,2,4-triazole nitrate; mp. 130.3° C;

1-[2-(2,4-dichlorophenyl)-4-hexyl-1,3-dioxolan-2-ylmethyl]-1H-1,2,4-triazole nitrate; mp. 106.2° C;

1-[2-(2,4-dichlorophenyl)-4-heptyl-1,3-dioxolan-2-ylmethyl]-1H-1,2,4-triazole nitrate; mp. 96.8° C; and 1-[2-(2,4-dichlorophenyl)-4-octyl-1,3-dioxolan-2-ylmethyl]-1H-1,2,4-triazole nitrate; mp. 110.6° C.

EXAMPLE XXXVII

A. 20.8 parts of 1-(9H-fluoren-2-yl)ethanone are dissolved in 240 parts of butanol. At a temperature of 50° C, 16 parts of bromine are added dropwise while the mixture is allowed to reach room temperature. After complete addition of bromine (1 hour), the whole is stirred at room temperature for 1 hour. Then there are added successively 7.5 parts of 1,2-ethanediol, 360 parts of benzene and 2 parts of 4-methylbenzenesulfonic acid. Stirring is continued overnight at reflux temperature with water-separator. After cooling to room temperature, the reaction mixture is evaporated. The residue is taken up in a mixture of 2,2'-oxybispropane and benzene (1:1 by volume). The resulting solution is washed successively with a diluted sodium hydroxide solution and three times with water, dried, filtered and evaporated. The residue is crystallized from methanol. The product is filtered off and dried, yielding 20.5 parts (62%) of 2-(bromomethyl)-2-(9H-fluoren-2-yl)-1,3-dioxolane; mp. 90° C.

B. To a stirred sodium methoxide solution, prepared starting from 2.3 parts of sodium in 48 parts of methanol, are added 6.9 parts of 1H-1,2,4-triazole. After stirring for 1 hour at room temperature, 135 parts of N,N-dimethylformamide are added. The methanol is distilled off at normal pressure till internal temperature of 130° C . Then there are added successively 20.5 parts of 2-(bromomethyl)-2-(9H-fluoren-2-yl)-1,3-dioxolane and 3 parts of potassium iodide and the whole is stirred and refluxed overnight. After cooling to room temperature, the reaction mixture is poured onto water. Upon scratching, the product is precipitated, filtered off and washed with water. The product, dissolved in trichloromethane, is purified by column-chromatography over silica gel using a mixture of trichloromethane and 5% of methanol as eluent. The pure fractions are collected and the eluent is evaporated. The residue is crystallized from a mixture of benzene and 2,2'-oxybispropane (1:1 by volume), yielding 3.9 parts (20%) of 1-[2-(9H-fluoren-2-yl)-1,3-dioxolan-2-ylmethyl]-1H-1,2,4-triazole; mp. 186.8° C.

We claim:

1. A chemical compound selected from the group consisting of a 1-(β-aryl)ethyl-1H-1,2,4-triazole ketal having the formula:

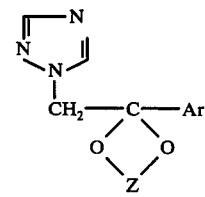

and the therapeutically active acid addition salts thereof, wherein:

Z is an alkylene selected from the group consisting of —CH$_2$—CH$_2$—, —CH$_2$—CH$_2$—CH$_2$—, —CH(CH$_3$)—CH(CH$_3$)— and —CH$_2$—CH(alkyl)—, wherein said alkyl has from 1 to 10 carbon atoms; and Ar is a member selected from the group consisting of phenyl, substituted phenyl, thienyl, 5 chloro-2-thienyl, naphthyl and fluorenyl, and wherein "substituted phenyl" has the meaning of a phenyl radical having thereon from 1 to 3 substituents selected independently from the group consisting of halo, loweralkyl, loweralkyloxy, cyano and nitro.

2. A member selected from the group consisting of 1-[2-(2,4-dichlorophenyl)-1,3-dioxolan-2-ylmethyl]-1H-1,2,4-triazole and the therapeutically active acid addition salts thereof.

3. A member selected from the group consisting of 1-[2-(2,4-dichlorophenyl)-4-methyl-1,3-dioxolan-2-ylmethyl]-1H-1,2,4-triazole and the therapeutically active acid addition salts thereof.

4. A member selected from the group consisting of 1-[2-(2,4-dichlorophenyl)-4-ethyl-1,3-dioxolan-2-ylmethyl]-1H-1,2,4-triazole and the therapeutically active acid addition salts thereof.

5. A member selected from the group consisting of 1-[2-(2,4-dichlorophenyl)-4-propyl-1,3-dioxolan-2-ylmethyl]-1H-1,2,4-triazole and the therapeutically active acid addition salts thereof.

6. A member selected from the group consisting of 1-[2-(2,4-dichlorophenyl)-4-pentyl-1,3-dioxolan-2-ylmethyl]-1H-1,2,4-triazole and the therapeutically active acid addition salts thereof.

* * * * *

UNITED STATES PATENT AND TRADEMARK OFFICE
CERTIFICATE OF CORRECTION

PATENT NO. : 4,079,062
DATED : March 14,1978
INVENTOR(S) : Gustaaf Van Reet, Jan Heeres, Lourens Wals It is certified that error appears in the above-identified patent and that said Letters Patent are hereby corrected as shown below:

At Column 7, Line 18, "barely" should be -- barley --.
At Column 7, Line 42, "o" should be -- of --.

At Column 12, Line 28, "power" should be -- powder --.
At Column 15, Line 25, "recipitated" should be -- precipitated--
At Column 16, Line 16, "recipitated" should be -- precipitated--
At Column 17, Line 14, "prepated" should be -- prepared --.
At Column 17, Line 45, "prepard" should be -- prepared --.
At Column 25, Line 44, after "130°C" insert -- . --.

Signed and Sealed this

Seventh Day of November 1978

[SEAL]

Attest:

RUTH C. MASON
Attesting Officer

DONALD W. BANNER
Commissioner of Patents and Trademarks